United States Patent [19]
Watanabe

[11] Patent Number: 4,721,098
[45] Date of Patent: Jan. 26, 1988

[54] GUIDING AND/OR MEASURING INSTRUMENT FOR ENDOSCOPE APPARATUS

[75] Inventor: Yoshio Watanabe, Kawaguchi, Japan

[73] Assignee: Kabushiki Kaisha Machida Seisakusho, Japan

[21] Appl. No.: 918,554

[22] Filed: Oct. 14, 1986

[30] Foreign Application Priority Data

Dec. 3, 1985 [JP] Japan .................. 60-185625
Jul. 7, 1986 [JP] Japan .................. 61-103241

[51] Int. Cl.⁴ ................................................ A61B 1/00
[52] U.S. Cl. ........................................ 128/4; 350/96.26
[58] Field of Search ................. 128/4, 6; 350/96.26

[56] References Cited

U.S. PATENT DOCUMENTS

| | | | |
|---|---|---|---|
| 4,530,568 | 7/1985 | Haduch et al. | 128/6 X |
| 4,575,185 | 3/1986 | Wentzell et al. | 128/6 X |
| 4,659,195 | 4/1987 | D'Amelio et al. | 128/6 X |

*Primary Examiner*—William H. Grieb

[57] ABSTRACT

In an endoscope apparatus, an inserting instrument is insertable through an inserting portion of an endoscope so as to have a distal end portion projected from a distal end of the inserting portion. The inserting instrument comprises an outer tubular envelope and an elongated rod-like member located at a distal end of the envelope. An operating device located at a proximal end of the envelope is connected to the rod-like member through a wire member extending through the envelope. The rod-like member is operated to be moved between an inoperative position where the longitudinal axis of the rod-like member extends substantially in coaxial relation to the envelope and an operative position where the longitudinal axis of the rod-like member extends across an extended line of the envelope. The inserting instrument may be utilized as guiding and/or measuring instrument. For the guiding instrument, the rod-like member located in the operative position is brought into engagement with an object to be inspected, to guide the inserting portion thereinto. For the measuring instrument, the rod-like member has carried thereon graduations for measurement.

12 Claims, 6 Drawing Figures

Fig.3
Fig.4
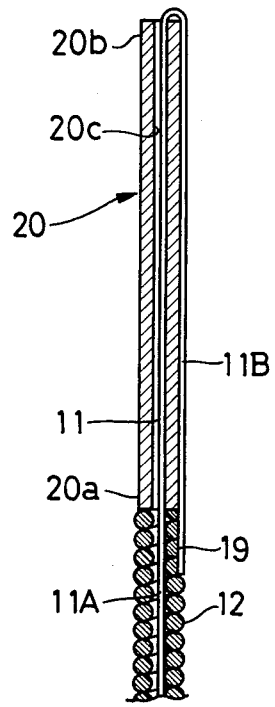
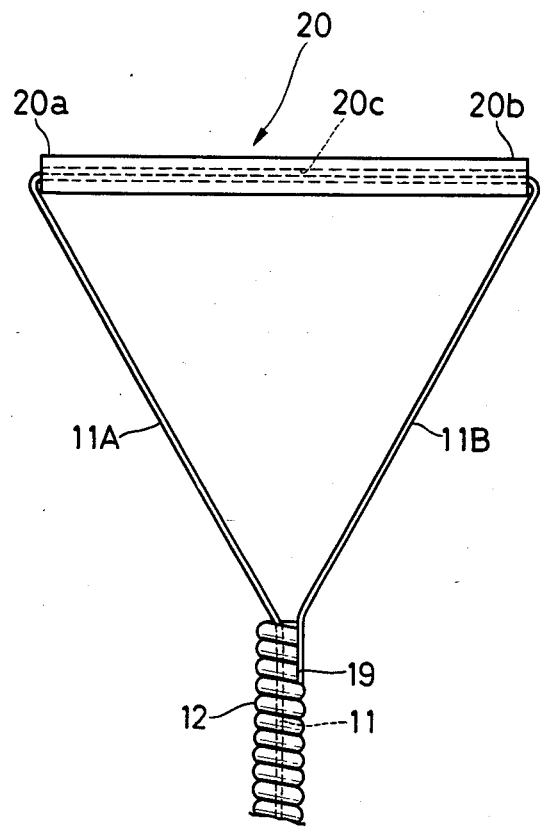

GUIDING AND/OR MEASURING INSTRUMENT FOR ENDOSCOPE APPARATUS

BACKGROUND OF THE INVENTION

The present invention relates to an industrial and/or medical endoscope apparatus and, more particularly, to an inserting instrument for such endoscope apparatus, which is utilized as a guiding instrument for guiding a flexible inserting portion of an endoscope into an object to be inspected and/or as a measuring instrument for measuring a size of a part within the object.

In recent years, an industrial endoscope apparatus has widely been utilized in various kinds of industrial fields. The reason for this is that, in the inspection and the like of an interior of a machine such as, for example, a jet engine, the interior of the machine as an object to be inspected can be viewed without disassembling the machine, and this makes it possible to reduce the working time and to improve the working performance or efficiency.

A general endoscope apparatus of this kind referred to above comprises an endoscope which includes an operating body and a flexible inserting portion extending from one end of the operating body. An ocular portion is provided at the other end of the operating body. In use, the inserting portion of the endoscope is inserted into an interior of an object to be inspected, through an opening provided in the object. The interior of the object is viewed by the ocular portion through a viewing optical system provided at the inserting portion.

In case where the interior of the object to be inspected is complicated in configuration and one or more restrictions are formed within the object on the way to a part to be inspected, however, should an attempt be made to insert the inserting portion alone, the distal end of the inserting portion would often sag under its own weight, because of the flexibility of the inserting portion, and it would be difficult to insert the inserting portion to the desired part to be inspected. In such case, it has conventionally been proposed that the inserting portion of the endoscope is inserted through a guide tube harder than the inserting portion; the guide tube is precedently passed through the restrictions while determining the passing direction of the guide tube by the inserting portion; and, subsequently, the inserting portion is advanced through the guide tube and is projected from the distal end of the guide tube, to permit the inserting portion to view the part to be inspected. However, the guide tube is required to have its outer diameter greater than that of the inserting portion, and the increase in diameter makes the inserting operation difficult accordingly. This would cause the operability to be deteriorated. In addition, if the diameter of the restrictions within the object to be inspected is less than that of the guide tube, it is no longer possible to use the guide tube.

In view of the above, a further proposal has been made in which a guide channel is formed which extends through the operating body and the inserting portion of the endoscope; a guiding instrument is inserted from an inserting opening provided in the operating body into and through the guide channel so as to have a distal end projected from the distal end of the inserting portion; an engaging member provided at the distal end of the guiding instrument is brought into engagement with the restriction within the object to be inspected; and, subsequently, the inserting portion of the endoscope is advanced along the guiding instrument. A known guiding instrument of this kind is comprised of a thin or fine tube and a balloon which is attached to a distal end of the tube and which serves as an engaging member. The balloon is maintained withered until the distal end of the guiding instrument reaches the restriction within the object to be inspected. Fluid such as water, air or the like is injected into the balloon to inflate the same when the distal end of the guiding instrument reaches the restriction, to thereby bring the inflated balloon into engagement with the restriction. Another known guiding instrument is comprised of a helical tube, and a hook which serves as an engaging member and which is attached to the distal end of the helical tube. The hook is brought into engagement with the restriction within the object to be inspected.

However, the above-described, conventional guiding instruments for the inserting portion of the endoscope have had the following problems:

In case of the guiding instrument employing the balloon, there is a problem in the durability of the balloon. Specifically, should the balloon be damaged and broken by sharp-pointed projections such as flashes or fins formed within the object, it would no longer be possible to inflate the balloon and this would make it impossible to bring the balloon into engagement with the restriction within the object.

In case of the guiding instrument employing the hook, it is not possible to vary or alter the configuration of the hook, unlike the balloon, before and after the engagement of the hook with the restriction and, therefore, it is extremely difficult to ensure the engagement of the hook with the restriction.

Apart from the above, it has often been desired and required to measure a size or dimension of a part such as polyp within a body cavity or a size of a part within a machine. A measuring instrument used for this purpose is disclosed in Japanese Utility Model Application Laid-Open No. 57-7501 laid open to public inspection on Jan. 14, 1982, for example. The measuring instrument disclosed in the Japanese utility model application comprises an outer tubular envelope, a wire extending through the envelope, a pair of elongated, curved spring members having their respective one ends connected to a distal end of the wire and the respective other ends spaced away from each other, and a collapsible or foldable strap-like scale having carried thereon graduations and extending between the respective other ends of the spring members.

In use of the measuring instrument, the inserting portion of the endoscope is inserted into an object to be inspected and the distal end of the inserting portion is located adjacent a part to be measured. Subsequently, under such a condition that the pair of spring members and the scale are previously retracted into the distal end of the outer envelope so that the other ends of the respective spring members are located close to each other against their respective spring forces and the scale is collapsed or folded, the outer envelope is inserted from the inserting opening provided in the operating body of the endoscope, into and through the inserting portion thereof so as to have the distal end projected from the distal end of the inserting portion. Subsequently, the wire is operated to project the spring members from the distal end of the outer envelope. The other ends of the respective spring members are spaced apart away from each other under their respective spring forces to allow the strap-like scale to be stretched straight. The stretched scale is approached to the part to be measured, and the graduations on the scale are viewed and read through a viewing optical system at the distal end of the inserting portion.

Since, however, it is necessary for the abovedescribed conventional measuring instrument for the endoscope, to retract and house the scale and the spring members into and within the distal end of the envelope, the diameter of the envelope is inevitably increased. This results in an enlargement of the diameter of the inserting portion of the endoscope through which the envelope is inserted.

OBJECT AND SUMMARY OF THE INVENTION

An object of the present invention is to provide an endoscope apparatus which can solve at least one of the problems discussed above.

According to the invention, there is provided an endoscope apparatus comprising:

an endoscope including an operating body provided therein with an inserting opening, a inserting portion extending from the operating body and adapted to be inserted into an object to be inspected, and a guide channel extending through the operating body and the inserting portion and in communication with the inserting opening;

an elongated inserting instrument insertable from the inserting opening into and through the guide channel so as to have a distal end portion projected from a distal end of the inserting portion;

the elongated inserting instrument comprising a yieldable tubular envelope having proximal and distal ends thereof respectively located adjacent the operating body and the distal end of the inserting portion when the inserting instrument is inserted from the inserting opening into and through the guide channel, fixed wire means having one end thereof fixedly secured to the distal end of the tubular envelope, an elongated rodlike member having one end thereof connected to the other end of the fixed wire means, push-pull wire means extending through the tubular envelope, the push-pull wire means having one end thereof connected to the other end of the rod-like member and the other end projecting from the proximal end of the tubular envelope, and an operating member connected to the other end of the push-pull wire means; and the operating member being movable relative to the proximal end of the tubular envelope for pushing and pulling the push-pull wire means so as to move the rod-like member between an inoperative position where the rod-like member has its longitudinal axis extending substantially in coaxial relation to the tubular envelope and an operative position where the rod-like member has its longitudinal axis extending across an extended line of the tubular envelope.

BRIEF DESCRIPTION OF THE DRAWINGS

FIG. 3 is a fragmental cross-sectional view showing, in an enlarged scale, a distal end of the inserting instrument shown in FIG. 1, in which a rod-like member serving as an engaging member is located in an inoperative position;

FIG. 4 is a fragmental view showing the rod-like member illustrated in FIG. 3, but located in an operative position;

DETAILED DESCRIPTION

Figure 1:
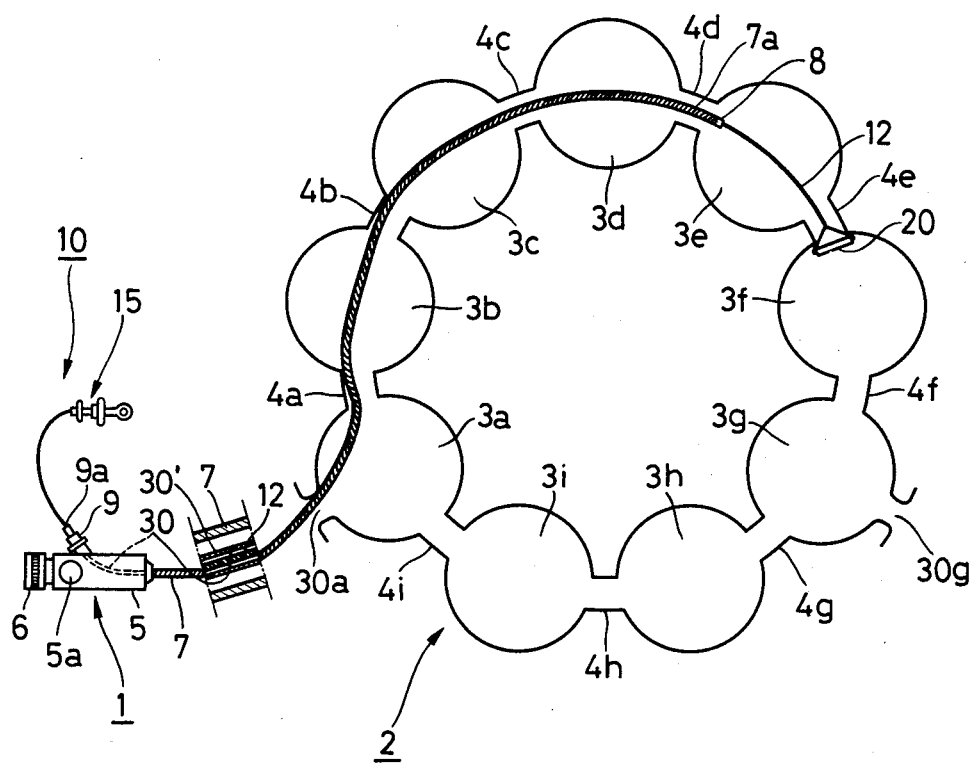
FIG. 1 is a schematic view showing an endoscope apparatus in accordance with an embodiment of the invention, in which an inserting instrument is utilized as a guiding instrument for guiding an inserting portion of an endoscope into a jet engine.

The invention will now be described, by way of an example, with reference to the drawings in which like reference numerals are used throughout to designate like or similar parts or components.

Referring to FIGS. 1 through 4, in particular, to FIG. 1, there is shown an endoscope apparatus in accordance with an embodiment of the invention, which is illustrated as being employed to view an interior of an object to be inspected, i.e., a jet engine 2. The jet engine 2 has first to ninth combustion chambers 3a-3i each having a circular cross-section. Each pair of adjacent combustion chambers are connected to each other by a corresponding one of connecting pipes or restrictions 4a-4i, so that the combustion chambers 3a-3i are connected to each other in the form of a ring. Two 3a and 3g of the nine combustion chambers 3a-3i are provided with bores 30a and 30g respectively, in each of which an ignition plug is adapted to be mounted. Flames generated within the combustion chambers 3a and 3g by the ignition plugs are passed around all of the combustion chambers 3a-3i through the connecting pipes 4a-4i. When it is desired to inspect the interior of the engine, the ignition plugs are removed respectively from the bores 30a and 30g so that the bores can be utilized for the insertion of the endoscope apparatus.

The endoscope apparatus comprises an endoscope 1 which is known per se, and which includes an operating body 5, an ocular portion 6 provided at one end of the operating body 5, and a flexible inserting portion 7 extending from the other end of the operating body 5. The inserting portion 7 has, adjacent a distal end thereof, a bendable section 7a which has a curvature remote-controllable by a dial 5a at the operating body 5. A hard or rigid tip component 8 is provided at an end of the bendable section 7a, adjacent the distal end of the inserting portion 7. The tip component 8 has an end face which is provided therein with a viewing window and an illuminating window, both not shown. A guide 9 having therein an inserting opening 9a is mounted to the operating body 5 and extends outwardly therefrom at a predetermined angle of inclination with respect to the operating body 5. The inserting opening 9a is in communication with a guide channel 30 defined by a tube 30 incorporated into the operating body 5 and the inserting portion 7. The guide channel 30 opens at the end face of the tip component 8.

The endoscope apparatus further comprises an elongated inserting instrument generally designated by the reference numeral 10. The inserting instrument 10, serving as a guding instrument in the instant embodiment, is insertable from the inserting opening 9a into and through the guide channel 30 so as to have a distal end portion projected from the distal end of the inserting portion 7. The inserting instrument 10 comprises a yieldable tubular envelope formed by a helical tube 12 having proximal and distal ends thereof respectively located adjacent the operating body 5 and the distal end of the inserting portion 7 when the inserting instrument 10 is inserted from the inserting opening 9a into and through the guide channel 30. A single continuous wire member 11 shown in FIG. 2 extends through the helical tube 12. A remote-operating device 15 is provided at the proximal end of the helical tube 12. Specifically, the remote-operating device 15 comprises a stopper member 13 fixedly secured to the proximal end of the helical tube 12, and an elongated rod 14 fixedly connected to the stopper member 13 so as to extend from a proximal end face 13a thereof away from the proximal end of the helical tube 12 substantially in coaxial relation thereto. The stopper member 13 serves as a finger engaging member as will be described later. The rod 14 has an elongated guide slot 14a formed therein. A ring 16 is fixedly connected to an end of the rod 14 remote from the stopper member 13. An operating member or slider 17 is mounted on the rod 14 for sliding movement therealong. A pin 18 is fixedly mounted to the slider 17 so as to extend through the guide slot 14a. The wire member 11 extending through the helical tube 12 and the stopper member 13 has one end fixedly connected to the pin 18.

As shown in FIGS. 3 and 4, a cut-out 19 having a depth substantially equal to a diameter of the wire member 11 is formed at the outer periphery of the distal end of the helical tube 12. The wire member 11 has a distal end portion thereof which projects from the distal end of the helical tube 12, extends through a longitudinal through bore 20c formed in an elongated, metallic rod-like engaging member 20, and is fixedly secured to the cut-out 19 on the helical tube 12 by means of weld, adhesion or the like. The wire member 11 is fixedly secured to the wall surface of the through bore 20c at the opposite ends 20a and 20b of the rod-like member 20, by means of weld or the like. The single continuous wire member 11 is comprised of a fixed wire section 11B extending from the end 20b of the rod-like member 20 to the cut-out 19 on the helical tube 12, and a push-pull wire section 11A extending from the slider 17 to the other end 20a of the rod-like member 20. The fixed wire section 11B has a length from the end 20b of the rod-like member 20 to the distal end face of the helical tube 12, which is substantially equal to the length of the rod-like member 20. The rod-like member 20 has a circular cross-section which is set such that the total sum of the cross-sectional outer dimension of the rod-like member 20 and the cross-sectional outer dimension of the fixed wire section 11B is less than the cross-sectional outer dimension of the helical tube 12.

Figure 2:
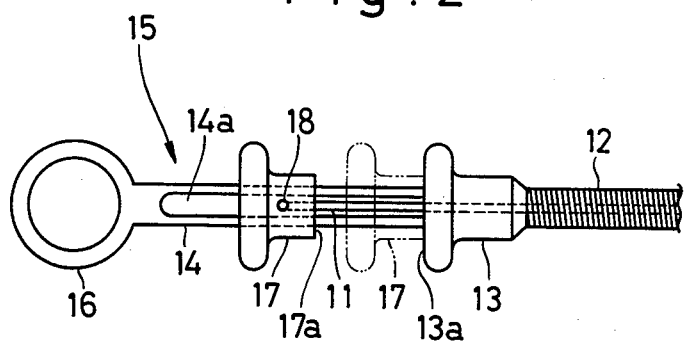
FIG. 2 is a fragmental view showing a remote-operating device of the inserting instrument illustrated in FIG. 1.

The slider 17 is slidable along the rod 14 relative to the stopper member 13 between a first position indicated by the solid lines in FIG. 2 where a distal end face 17a of the slider 17 is spaced from the proximal end face 13a of the stopper member 13, and a second position indicated by the two-dot-and-dash lines in FIG. 2 where the distal end face 17a abuts against the proximal end face 13a. When the slider 17 is moved from the first to the second position, the push-pull wire section 11A is pushed and is projected from the distal end of the helical tube 12. A portion of the push-pull wire section 11A projected from the distal end of the helical tube 12 when the slider 17 is moved to the second position has a length from the distal end face of the helical tube 12 to the other end 20a of the rod-like member 20, which is substantially equal to the length of the rod-like member 20. Thus, when the slider 17 is located in the second position, the rod-like member 20 is moved to an operative position shown in FIG. 4 where a generally triangular form is defined by the portion of the push-pull wire section 11A projected from the distal end of the helical tube 12, the rod-like member 20, and the fixed wire section 11B, so that the longitudinal axis of the rod-like member 20 extends substantially perpendicularly to an extended line of the helical tube 12.

When the slider 17 is moved from the second to the first position, the push-pull wire section 11A is pulled, and the portion thereof projected from the distal end of the helical tube 12 is retracted into the helical tube 12, as shown in FIG. 3. The end 20a of the rod-like member 20 is caused to abut against the distal end of the helical tube 12, and the rod-like member 20 is located in an inoperative position where the longitudinal axis of the rod-like member 20 extends substantially in coaxial relation to the helical tube 12, i.e., in straight relation thereto. That is, the stroke length of the slider 17 is made substantially equal to the length of the rod-like member 20.

The operation of the endoscope apparatus constructed as above will be described. The slider 17 is located in the first position where the rod-like member 20 extends in coaxial relation to the helical tube 12 as shown in FIG. 3. The inserting instrument 10 is then inserted from the inserting opening 19a into and through the guide channel 30 so as not to project the rod-like member 20 from the distal end of the inserting portion 7 of the endoscope 1. Subsequently, as shown in FIG. 1, the inserting portion 7 is inserted into the first combustion chamber 3a of the jet engine 2 through the bore 30a, and the interior of the first combustion chamber 3a is viewed by the ocular portion 6 through an optical transmitting system incorporated in the endoscope 1. At the viewing or observation, since the distal end of the inserting instrument 10 is housed in the guide channel 30, the distal end of the inserting instrument 10 does not interfere with the viewing of the interior of the first combustion chamber 3a. Subsequently, when it is desired to view the second combustion chamber 3b adjacent the first combustion chamber 3a, it is required to pass the inserting portion 7 through the connecting pipe 4a. In this case, with the bendable section 7a of the inserting portion 7 being maintained located in the first combustion chamber 3a, only the inserting instrument 10 is projected forwardly from the tip component 8. While ascertaining the position of the distal end of the inserting instrument 10 by the ocular portion 6 of the endoscope 1, an operator remotely operates the bendable section 7a to direct the distal end of the inserting instrument 10 toward the connecting pipe 4a. The operator further projects the inserting instrument 10 and inserts the distal end thereof into and through the connecting pipe 4a, to thereby allow the distal end of the inserting instrument 10 to enter the second combustion chamber 3b. At this time, since the rod-like member 20 is located in coaxial relation to the helical tube 12, it is possible to smoothly insert the distal end of the inserting instrument 10 through the connecting pipe 4a having a relatively small cross-sectional area.

After the insertion of the distal end of the inserting instrument 10 into the second combustion chamber 3b in the manner as described above, the operator clamps the stopper member 13 of the inserting instrument 10 between his forefinger and middle finger and brings his thumb into engagement with the slider 17, to thereby push the slider 17 toward the second position indicated by the two-dot-and-dash lines in FIG. 2. Then, the push-pull wire section 11A is pushed and advanced, and the distal end of the push-pull wire section 11A is projected from the distal end of the helical tube 12. Thus, as shown in FIG. 4, the rod-like member 20 is moved to the operative position where it cooperates with the fixed wire section 11B and the portion of the push-pull wire section 11A projected from the distal end of the helical tube 12, to define a generally triangular form.

Subsequently, the inserting instrument 10 is slightly pulled while maintaining the slider 17 in engagement with the stopper member 13. Then, respective parts, adjacent the distal end of the helical tube 12, of the fixed wire section 11B and of the portion of the push-pull wire section 11A projected from the distal end of the helical tube 12 are retracted into the connecting pipe 4a, whereby the opposite ends 20a and 20b of the rod-like member 20 are brought into engagement with the inner wall surface of the second combustion chamber 3b. The fixed wire section 11B and the portion of the push-pull wire section 11A projected from the distal end of the helical tube 12 perform a guiding action while being in contact with an end, adjacent the second combustion chamber 3b of the inner peripheral surface of the connecting pipe 4a. This allows the distal end of the helical tube 12 to be located on the central axis of the connecting pipe 4a and, in addition thereto, the distance from the end 20a of the rod-like member 20 to a point of intersection between the extended line of the helical tube 12 and the longitudinal axis of the rod-like member 20 and the distance from the end 20b of the rod-like member 20 to the point of intersection are made equal to each other. Thus, it is possible to bring the rod-like member 20 into positive engagement with the inner wall surface of the second combustion chamber 3b. In this manner, the rod-like member 20 in the instant embodiment serves as an engaging member.

Furthermore, during the pulling of the inserting instrument 10 in the manner as described above, the slider 17 is maintained in engagement with the stopper member 13, and no relative movement is caused to occur between the push-pull wire section 11A and the helical tube 12. Accordingly, the push-pull wire section 11A serves as a reinforcement to prevent the helical tube 12 from being stretched. In addition, since the push-pull wire section 11A and the helical tube 12 are both brought into a tensioned condition, it is possible to considerably increase the tension strength of the inserting instrument 10.

Subsequently, the inserting portion 7 of the endoscope 1 is advanced along the helical tube 12 of the inserting instrument 10. Thus, the inserting portion 7 is inserted into the second combustion chamber 3b smoothly for a short period of time.

Subsequently, with the inserting portion 7 being located in the second combustion chamber 3b, the entire inserting instrument 10 is slightly advanced. Thereafter, the operator clamps the slider 17 between his forefinger and middle finger and inserts his thumb into the ring 16. The operator pulls the slider 17 toward the ring 16, i.e., toward the first position, to retract the portion of the push-pull wire section 11A which has been projected from the distal end of the helical tube 12, into the same.

As the slider 17 is located in the first position indicated by the solid lines in FIG. 2, the rod-like member 20 is moved to the inoperative position shown in FIG. 3 where the rod-like member 20 is brought into coaxial relation to the helical tube 12. Subsequently, the inserting instrument 10 is pulled to retract the rod-like member 20 into the guide channel 30 in the inserting portion 7, and the interior of the second combustion chamber 3b is viewed by the ocular portion 6 of the endoscope 1.

In this manner, the above-described operations are repeated, and this makes it possible to inspect all of the combustion chambers 3a–3i of the jet engine 2 for an extremely short period of time and easily.

Since the push-pull wire section 11A and the fixed wire section 11B of the inserting instrument 10 are fixedly secured to the rod-like member 20, should the push-pull wire section 11A or the fixed wire section 11B be broken or severed, it would be possible to prevent some components of the inserting instrument 10 from being left within the jet engine 2, and it would be possible to remove such components out of the jet engine 2.

In the embodiment described above, since the push-pull wire section 11A and the fixed wire section 11B are formed by the single continuous wire member 11, it may be sufficient if the wire member 11 is fixedly secured to the rod-like member 20 at a single location. Of course, the push-pull wire section 11A and the fixed wire section 11B may be formed by separate wires, respectively.

As descrived above, according to the embodiment of the invention shown in FIGS. 1 through 4, the distal end of the inserting instrument 10 has the cross-sectional area less than that of the inserting portion 7 of the endoscope 1. Accordingly, even if the restrictions or connecting pipes 4a–4i having the relatively small cross-sectional area are present on the way to a part to be viewed within the object to be inspected or jet engine 2, it is possible to easily and positively insert the distal end of the inserting instrument 10 antecedent to the inserting portion 7, through the restrictions or connecting pipes 4a–4i. Further, after the insertion of the distal end of the inserting instrument 10 into the jet engine 2, the rod-like member 20 can be located so as to have the longitudinal axis thereof extending perpendicularly to the extended line of the outer envelope or helical tube 12 so that the distance from one end 20a of the rod-like member 20 to a point of intersection between the rod-like member 20 and the extended line of the helical tube 12 and the distance from the other end 20b of the rod-like member 20 to the point of intersection are made substantially equal to each other. This makes it possible to prevent the rod-like 20 from being disengaged from the interior of the jet engine 2, to thereby ensure that the inserting portion 7 of the endoscope 1 is guided through the restrictions or connecting pipes 4a–4i.

Moreover, since the inserting instrument 10 is pulled while the slider 17 is maintained in engagement with the stopper member 13, the push-pull wire section 11A and the helical tube 12 are both brought into a tensioned condition. This increases the tension strength of the inserting instrument 10.

Furthermore, when the interior of the jet engine 2 is viewed by the endoscope 1, the distal end of the inserting instrument 10 can be housed in the inserting portion 7 of the endoscope 1. Thus, the distal end of the inserting instrument 10 does not interfere with the viewing or observation.

In addition, since it is possible to reduce the number of components of the inserting instrument 10, the construction thereof can be simplified. A possibility of troubles or falts is reduced. The operability is improved. This makes it possible to reduce the working time and cost.

Figure 5:
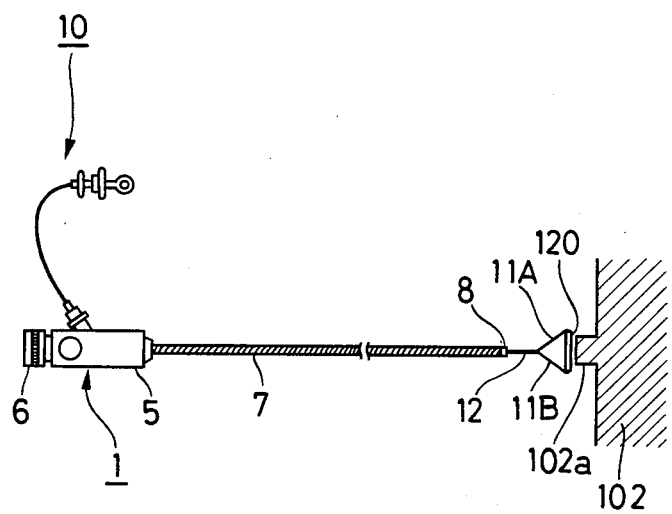
FIG. 5 is a schematic view showing another embodiment of the invention, in which an inserting instrument is utilized as a measuring instrument for measuring a part within an object to be inspected.
Figure 6:
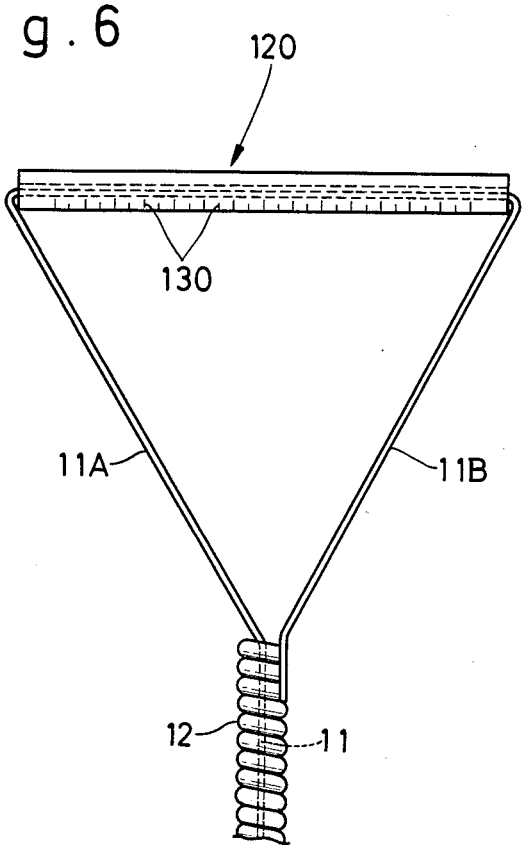
FIG. 6 is a fragmental enlarged view showing a distal end of the inserting instrument shown in FIG. 5, in which a rod-like member serving as a scale member having carried thereon graduations for measurement is located in an operative position.

FIGS. 5 and 6 show another embodiment of the invention, in which an endoscope apparatus is employed to measure a size of a part or parts within an object to be inspected. The endoscope apparatus shown in FIGS. 5 and 6 is substantially identical in construction with the endoscope apparatus shown in FIGS. 1 through 4, except that a rod-like member 120 serving as a scale member has carried thereon graduations 130 for measurement. In FIGS. 5 and 6, like reference numerals are used to designate parts and components similar to those shown in FIGS. 1 through 4, and the description of such similar parts and components will not therefore be repeated here to avoid the duplication.

When it is desired to measure a size or dimension of a part to be measured 102a within an object to be inspected 102, such as, for example, polyp within a body cavity or a part within a machine, the distal end of the inserting instrument 10 serving as a measuring instrument in the instant embodiment is projected from the tip component 8 of the inserting portion 7, and the rod-like member 120 is moved to the operative position shown in FIG. 6 where the longitudinal axis of the rod-like member 120 extends perpendicularly to the extended line of the helical tube 12, in a manner similar to that described with reference to FIGS. 1 through 4. Subsequently, the rod-like member 120 is caused to abut against the part to be measured 102a, and the graduations 130 are read by the ocular portion 6.

According to the embodiment shown in FIGS. 5 and 6, because of the rod-like member 120, it is possible to prevent the rod-like member 120 from being bent or folded, even if the rod-like member 120 is urged against the part to be measured 102a. Thus, it is possible to accurately measure the size of the part to be measured 102a.

In addition, the viewing direction from the viewing window provided at the tip component 8 is perpendicular to the rod-like member 120. This also makes it possible to accurately measure the size of the part to be measured 102a.

After the measurement, the rod-like member 120 is moved to the inoperative position where the longitudinal axis thereof extends in coaxial relation to the helical tube 12, as described and shown with reference to FIG. 3. Subsequently, the distal end of the inserting instrument 10 is retracted into and housed within the guide channel 30 (FIG. 1), and the inserting portion 7 of the endoscope 1 is pulled out of the object to be inspected 102.

Of course, it is possible to utilize the rod-like member 120 as the engaging member described with reference to FIGS. 1 through 4, so that the inserting instrument 10 serves also as a guiding instrument.

As described above, according to the embodiment shown in FIGS. 5 and 6, it is not required to house the rod-like member 120 into the helical tube 12. This makes it possible to reduce the cross-sectional dimension of the helical tube 12, and also to simplify the construction of the distal end of the inserting instrument 10.

Althrough the embodiments of the invention have been described as having the rod-like member 20, 120 which is located in the operative position where the longitudinal axis thereof extends perpendicularly to the extended line of the helical tube 12 when the slider 17 is located in the second position, it should be appreciated that this is not essential to the invention, but it is sufficient if the longitudinal axis of the rod-like member 20, 120 extends across the extended line of the helical tube 12 when the slider 17 is located in the second position.

In addition, although the embodiments have been described as having the slider 17 which is moved from the first position indicated by the solid lines in FIG. 2 to the second position indicated by the two-dot-and-dash lines in FIG. 2 to push the push-pull wire section 11A, to thereby locate the rod-like member 20, 120 in the operative position shown in FIG. 4 or 6, it should be appreciated that this is not also essential to the invention. That is, such an arrangement may be considered that when the slider 17 is moved from the first position indicated by the solid lines in FIG. 2 to the second position indicated by the two-dot-and-dash lines in FIG. 2, the push-pull wire section 11A is pushed to angularly move the end 20a of the rod-like member 20, 120 away from the distal end of the helical tube to thereby locate the rod-like member 20, 120 in the inoperative position where the rod-like member extends substantially in coaxial relation to the helical tube 12, and when the slider 17 is moved from the second to first position, the push-pull wire section 11A is pulled to locate the rod-like member in the operative position where the rod-like member extedns substantially perpendicularly to the extended line of the helical tube 12.

The invention should not be limited to the specific embodiments described above, but various changes and modifications may be made to the invention. For example, the outer envelope should not be limited to the helical tube, but may be any one of tubular members which are yieldable and have a certain degree of rigidity. In addition, the rod-like member should not be limited to one having a circular cross-section, but may have a rectangular cross-section and also may be formed of a resin.

What is claimed is:

1. An endoscope apparatus comprising:
    an endoscope including an operating body provided therein with an inserting opening, a inserting portion extending from said operating body and adapted to be inserted into an object to be inspected, and a guide channel extending through said operating body and said inserting portion and in communication with said inserting opening;
    an elongated inserting instrument insertable from said inserting opening into and through said guide channel so as to have a distal end portion projected from a distal end of said inserting portion;
    said elongated inserting instrument comprising a yieldable tubular envelope having proximal and distal ends thereof respectively located adjacent said operating body and said distal end of said inserting portion when said inserting instrument is inserted from said inserting opening into and through said guide channel, fixed wire means having one end thereof fixedly secured to said distal end of said tubular envelope, an elongated rod-like member having one end thereof connected to the other end of said fixed wire means, push-pull wire means extending through said tubular envelope, said push-pull wire means having one end thereof connected to the other end of said rod-like member and the other end projecting from said proximal end of said tubular envelope, and an operating member connected to the other end of said push-pull wire means; and said operating member being movable relative to said proximal end of said tubular envelope for pushing and pulling said push-pull wire means so as to move said rod-like member between an inoperative position where said rod-like member has its longitudinal axis extending substantially in coaxial relation to said tubular envelope and an operative position where said rod-like member has its longitudinal axis extending across an extended line of said tubular envelope.

2. An endoscope apparatus as defined in claim 1, wherein said operating member is movable relative to said proximal end of said tubular envelope between a first position where said rod-like member is located in said inoperative position and a second position where said rod-like member is located in said operative position, said push-pull wire means being pushed when said operating member is moved from said first to said second position, and said push-pull wire means being pulled when said operating member is moved from said second to said first position.

3. An endoscope apparatus as defined in claim 2, wherein said rod-like member has its longitudinal axis extending substantially perpendicularly to the extended line of said tubular envelope when said operating member is located in said second position.

4. An endoscope apparatus as defined in claim 3, wherein said fixed wire means has its length substantially equal to that of said rod-like member, and wherein a portion of said push-pull wire means projecting from said distal end of said tubular envelope when said operating member is located in said second position has a length substantially equal to that of said rod-like member.

5. An endoscope apparatus as defined in claim 4, wherein said rod-like member has carried thereon graduations for measurement.

6. An endoscope apparatus as defined in claim 4, wherein said rod-like member has its cross-sectional outer dimension less than that of said tubular envelope.

7. An endoscope apparatus as defined in claim 6, wherein the total sum of the cross-sectional outer dimension of said rod-like member and a cross-sectional outer dimension of said fixed wire means is less than the cross-sectional outer dimension of said tubular envelope.

8. An endoscope apparatus as defined in claim 7, including:

stopper means secured to said proximal end of said tubular envelope for stopping the movement of said operating member when the same is located in said second position.

9. An endoscope apparatus as defined in claim 8, including:

a rod extending from said stopper means away from said proximal end of said tubular envelope substantially in coaxial relation thereto; and said operating member being mounted on said rod for sliding movement therealong between said first and second positions.

10. An endoscope apparatus as defined in claim 1, wherein said push-pull wire means and said fixed wire means are comprised of a single continuous wire member, and wherein said rod-like member has formed therein a longitudinal through bore, said single continuous wire member extending through said through bore in said rod-like member and being fixedly secured thereto.

11. An endoscope apparatus as defined in claim 1, wherein said inserting portion of said endoscope is flexible, and said elongated inserting instrument serves to guide the insertion of said inserting portion of said endoscope into the object to be inspected.

12. An endoscope apparatus as defined in claim 1, wherein, when said rod-like member is moved to said inoperative position, the other end of said rod-like member abuts against the distal end of said tubular envelope.

* * * * *